(12) United States Patent
De Rigal et al.

(10) Patent No.: US 6,985,230 B2
(45) Date of Patent: Jan. 10, 2006

(54) COMPARISON SAMPLE FOR SIMULATING THE COLOR OF KERATINOUS ELEMENTS, AND RELATED METHODS

(75) Inventors: Jean De Rigal, Claye Souilly (FR); Christophe Dauga, Levallois-Perret (FR)

(73) Assignee: L'Oreal S.A., Paris (FR)

( * ) Notice: Subject to any disclaimer, the term of this patent is extended or adjusted under 35 U.S.C. 154(b) by 354 days.

(21) Appl. No.: 10/006,886

(22) Filed: Dec. 10, 2001

(65) Prior Publication Data

US 2002/0128780 A1 Sep. 12, 2002

(30) Foreign Application Priority Data

Dec. 8, 2000 (FR) ............................................ 00 16000

(51) Int. Cl.
*G01J 3/52* (2006.01)

(52) U.S. Cl. ........................................ 356/421; 356/422
(58) Field of Classification Search ................. 356/421, 356/422
See application file for complete search history.

(56) References Cited

U.S. PATENT DOCUMENTS

| | | | |
|---|---|---|---|
| 1,741,080 A | | 12/1929 | Stenz |
| 5,018,531 A | * | 5/1991 | Hartman ..................... 600/587 |
| 5,150,791 A | * | 9/1992 | Kamen et al. .............. 206/457 |
| 5,177,694 A | * | 1/1993 | Graham et al. ............. 356/421 |
| 5,311,293 A | | 5/1994 | MacFarlane et al. |
| 5,852,675 A | | 12/1998 | Matsuo et al. |
| 6,157,445 A | | 12/2000 | Macfarlane et al. |
| 6,594,388 B1 | * | 7/2003 | Gindele et al. ............. 358/520 |

FOREIGN PATENT DOCUMENTS

| | | |
|---|---|---|
| FR | 2 540 991 | 8/1984 |
| JP | 6-49321 | 7/1994 |
| JP | 6-51839 | 7/1994 |
| JP | 09-179561 | * 12/1995 |
| JP | 8-201174 | 8/1996 |
| JP | 9-133584 | 5/1997 |
| JP | 10-253459 | 9/1998 |
| JP | 11-272179 | 10/1999 |
| JP | 2001-74556 | 3/2001 |

OTHER PUBLICATIONS

Co-pending Application—Title: A Comparison Samples for Simulating an Appearance of A Keratinous Element, and Related Methods Inventor(s): Jen De Rigal et al. U.S. Filing Date: Dec. 10, 2001.
Patent Abstracts of Japan, vol. 017, No. 457, Aug. 20, 1993 (JP 05 107115 A).
Patent Abstracts of Japan, vol. 1997, No. 09, Sep. 30, 1997, (JP 09 133584 A).
English language Derwent Abstract of FR 2 540 991, Aug. 17, 1984.

* cited by examiner

*Primary Examiner*—F. L. Evans
*Assistant Examiner*—Kara Geisel
(74) *Attorney, Agent, or Firm*—Finnegan, Henderson, Farabow, Garrett & Dunner, LLP

(57) ABSTRACT

A system comprising a plurality of comparison samples each having a reflectance spectrum and being configured to substantially simulate a color of a keratinous element having a reflectance system. The reflectance spectrum of each comparison sample may be substantially similar to the reflectance spectrum of a respective keratinous element such that the comparison sample and the keratinous element appear to an observer to have substantially the same color under at least two differing illuminants.

219 Claims, 5 Drawing Sheets

FIG_1

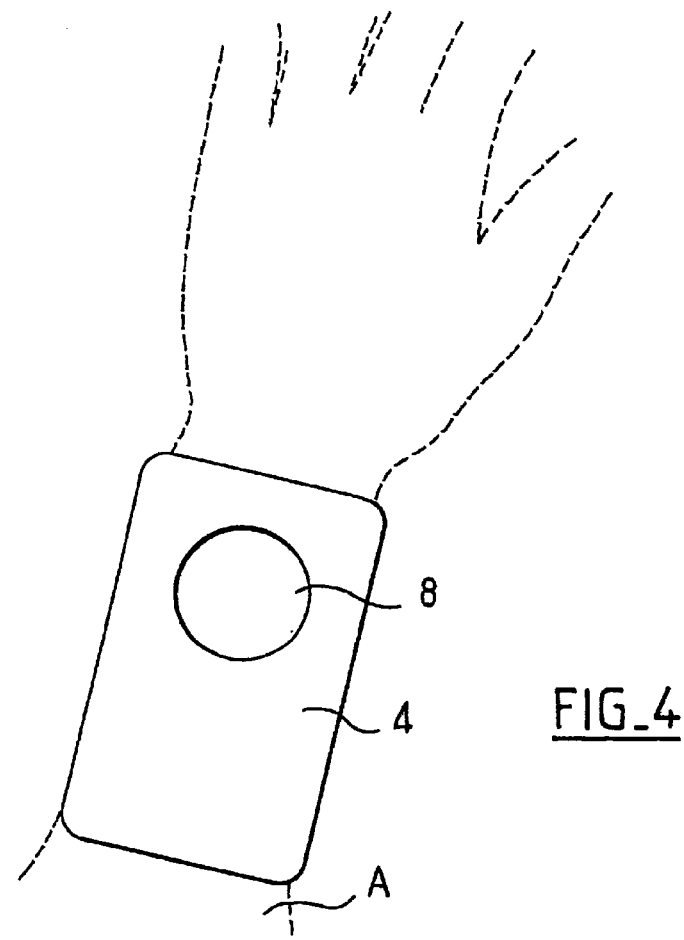
FIG_4
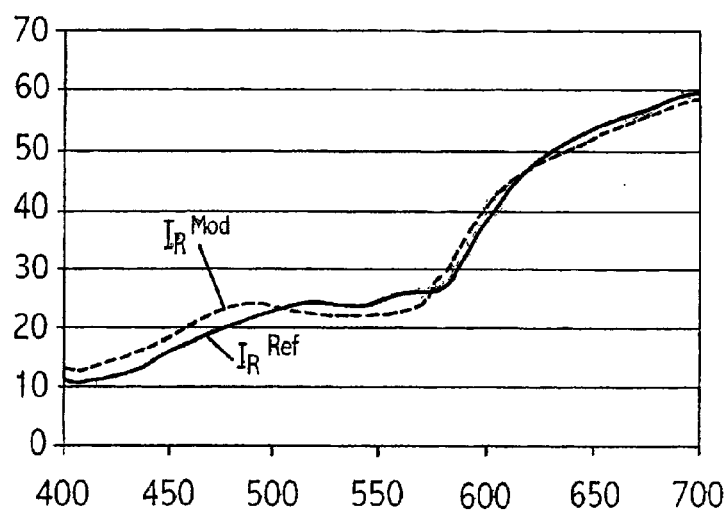
FIG_5

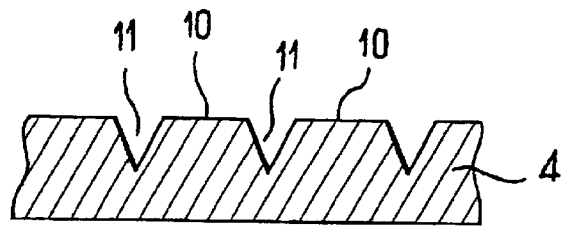
FIG_6
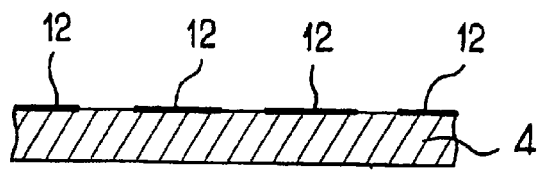
FIG_7
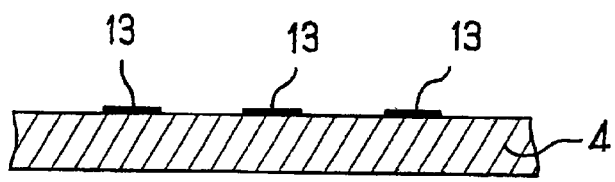
FIG_8
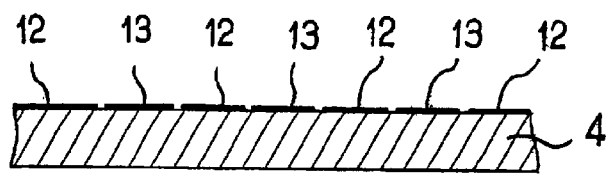
FIG_9
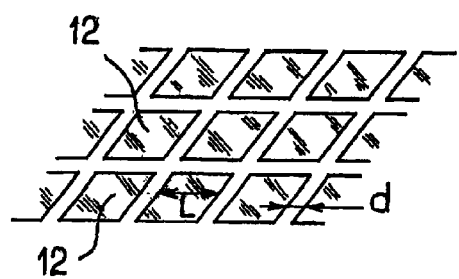
FIG_12

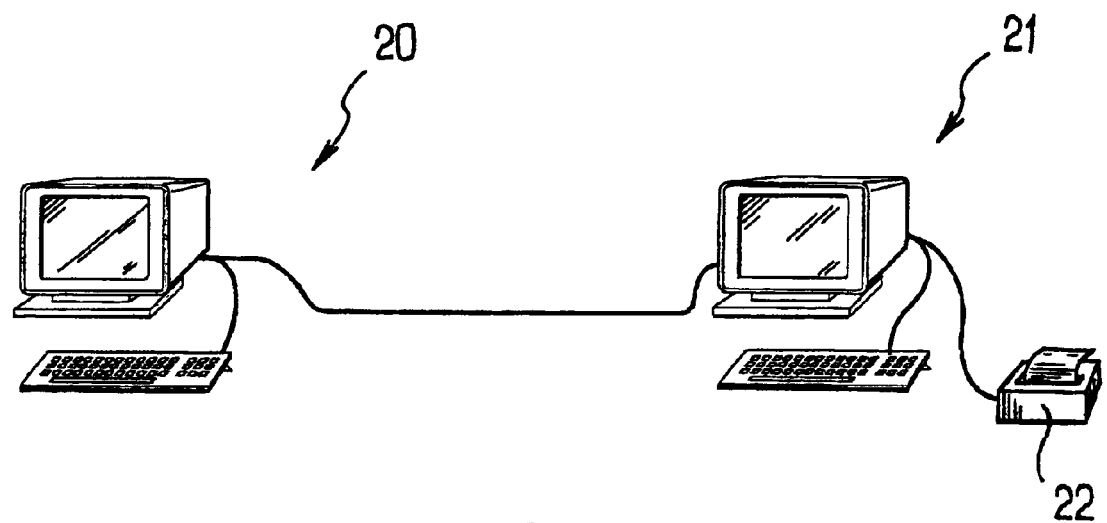
FIG_10
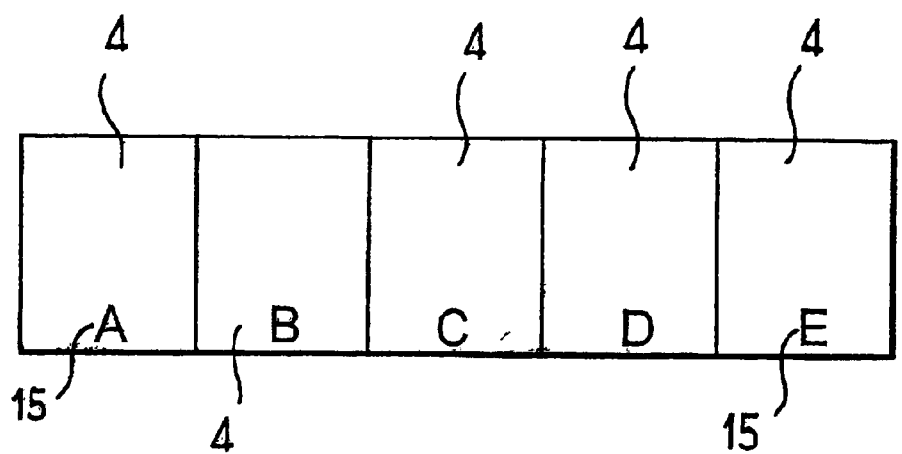
FIG.11

COMPARISON SAMPLE FOR SIMULATING THE COLOR OF KERATINOUS ELEMENTS, AND RELATED METHODS

The present invention relates to comparison samples configured to simulate the color of a keratinous element such as, for example the skin, including the lips, a fingernail, a toenail, or the hair.

Skin color is at least in part light back-scattered by the epidermis and by the dermis, which respectively contain varying amounts of the pigment melamine and varying amounts of hemoglobin.

The human eye may be extremely sensitive to the appearance of the skin, in particular its color, which often reflects the physical or emotional state of an individual.

There exists a need for samples that substantially simulate the color of a keratinous element such as, for example, the skin, including the lips, the fingernails, the toenails, or the hair, in a variety of environments, and, in particular, under differing kinds of lighting. The present invention seeks to satisfy this need.

It should be understood that the invention could be practiced without performing one or more aspects described. Other aspects will become apparent from the detailed description which follows.

As broadly described herein, an aspect of the invention includes a matching chart comprising at least one comparison sample substantially simulating the color of a keratinous element, such as the skin. Each comparison sample may comprise pigments and/or dyes selected in such a manner that a reflectance spectrum of the sample is substantially similar to a reflectance spectrum of the keratinous element. The element and the comparison sample may appear to an observer to have substantially the same color under at least two differing illuminants.

In another aspect, a system comprises a plurality of comparison samples, each comparison sample having a reflectance spectrum and being configured to substantially simulate a color of a keratinous element having a reflectance spectrum. The reflectance spectrum of each comparison sample may be substantially similar to the reflectance spectrum of a respective keratinous element such that the comparison sample and the keratinous element appear to an observer to have substantially the same color under at least two differing illuminants.

A user of the comparison sample, such as beautician, a clinician, or a dermatologist, or a person without any particular qualification in cosmetics, can, under a given illuminant, select a comparison sample that corresponds to a skin color and be substantially assured that the result of the selection will continue to be valid under some other illuminant.

The comparison samples may substantially simulate the color of the keratinous element under at least two of the illuminants, which may include D65 (daylight); D50; and A (incandescent lamp), for example.

According to an aspect, the color difference induced by changing illuminant is less than 4 and preferably less than 2.

At least some embodiments may facilitate evaluation of the color of a keratinous element without using a lighting system that has a specific emission spectrum.

In one embodiment, the reflectance spectrum of each comparison sample remains substantially similar to the corresponding keratinous element in a spectral range preferably extending from 400 nanometers (nm) to 800 nm.

For example, $$1/N(\lambda) \sum_{\lambda} |I_R^{MOD}(\lambda) - I_R^{REF}(\lambda)| / I_R^{REF}(\lambda)$$

(where $I_R^{MOD}(\lambda)$ is the reflected light intensity at wavelength $\lambda$ for the comparison sample, and $I_R^{REF}(\lambda)$ is the reflected light intensity at the wavelength $\lambda$ for the keratinous element) may be less than or equal to 0.1, less than 0.05, and/or less than 0.01.

When a plurality of comparison samples are provided, the comparison samples may present differing hues. The hue angles may range from approximately 40° to approximately 70°, and/or from approximately 46° to approximately 64°, in the CIEL*C*h 1976 color space.

By way of example, a system can comprise at least two categories of comparison sample, each having a determined hue, differing from the hue of the other categories.

The comparison samples can also have differing lightnesses. Lightness levels (L* in the CIEL*C*h 1976 color space) may range from about 34 to about 75. For example, there may be ten differing lightness levels in the plurality of comparison samples.

The comparison samples may have differing chroma levels. The chroma level of each comparison sample may range from about 12 to about 30, and may be about 22.

The system may comprise, for example, at least five categories of comparison samples, each having a hue that differs from the hue of the other categories.

In a preferred embodiment, the system of comparison samples comprises fifty colors corresponding to combining five hues and ten lightness levels.

The overall color difference $\Delta *E\ C*h.94$ as measured in the CIEL*C*h 1976 color space between two comparison samples corresponding to adjacent skin colors may be substantially constant. This difference may range from about 1 to about 40, from about 1 to about 20, and/or be about 4.

Within a given comparison sample, color can be substantially uniform and constant over at least part, and perhaps the entire, surface of the comparison sample, or it can be non-uniform, for example, so as to imitate the texture of the skin. A comparison sample can comprise two color coatings of different colors, the combination producing an average color for the eye.

The pigments and/or dyes used may be selected, where appropriate, as a function of the incidence on the final color of juxtapositions or superpositions of various colors on the comparison sample.

A comparison sample can also receive a color coating on a support that is not smooth and whose relief is selected in such a manner as to imitate the grain (or texture) of the keratinous element.

Each of the comparison samples can comprise a support, for example having a generally rectangular in shape. The support may dimensions of approximately 60 millimeters (mm) by 100 mm.

The support may have a hole. The hole may be located at about one-third of the way along the support's length. The hole may have a dimension of about 20 mm. As an example, the hole may be circular and have a diameter of about 20 mm.

A plurality of comparison samples can be in the form of a set of comparison samples connected together to form a fan-like configuration. The plurality of comparison samples can be on a common support, which may be in the form of a strip, for example. For instance, five comparison samples may be juxtaposed on the strip.

Each comparison sample may have an identifier, such as an alphanumeric code, for example, associated with it. The identifier may be associated with the color of the sample. This may enable a user to identify the various comparison samples relatively easily.

The comparison samples may be non-uniform in brightness or shine, such as when they simulate the appearance of the skin, for example the way the skin may be locally relatively shinier or less shiny (i.e., relatively dull).

The comparison samples can thus comprise a surface with adjacent regions having differing amounts of shine. The relatively shiny regions may comprise a gloss varnish while the relatively dull regions may comprise a mat varnish. The width of the relatively shiny regions can be about 300 micrometers ($\mu$m) and the width of the relatively dull regions can be about 100 $\mu$m. These dimensions may be particularly suitable for simulating skin.

Each comparison sample also may substantially simulate at least one appearance characteristic other than color, such as, for example brightness, relief, or non-uniformity of color.

At least two comparison samples of differing brightnesses, of differing amounts of relief, and/or of different color distributions within each sample may be provided.

The degree of brightness may be obtained by means of varnishes of various amounts of gloss, or may be achieved by means of determined surface relief.

The comparison samples may be substantially uniform in brightness.

Each comparison sample may be configured to be provided on a packaging for a product intended for application to a keratinous element. For example, the comparison sample can be printed on the packaging or can be affixed thereto.

The pigments and/or dyes for use in making the coating for a comparison sample may be selected as a function of the incidence on the final color of the treatment that is implemented.

Where appropriate, the comparison sample can receive printing both of a mat varnish and of a gloss varnish.

The comparison sample may be configured to be displayed via an electronic image.

The comparison samples may make it possible, for example, to prevent a person attending a solarium (or otherwise tanning) from pointless exposure to ultraviolet radiation once a desired degree of suntan has been reached or has nearly been reached. Such a method may facilitate quantification of the variation in skin color following a given treatment, and in turn may facilitate evaluation of the effectiveness of the treatment.

According to another aspect, the invention includes a method of making a comparison sample configured to substantially simulate the color of a keratinous element. The method may comprise depositing a coating on a support, wherein the coating has a reflectance spectrum that is substantially similar to a reflectance spectrum of a keratinous element, such that the comparison sample and the keratinous element appear to an observer to have substantially the same color under at least two differing illuminants.

The method may further comprise treating at least one of the support and the coating to imitate a texture of the keratinous element. The treating may comprise embossing or printing patterns on a background, the patterns and the background having differing colors. The treating also may comprise applying a mat varnish or a gloss varnish.

According to yet another aspect, a method of manufacturing a product intended for application to a keratinous element comprises providing a system of comparison samples, such as described above, selecting at least one of a plurality of comparison samples, and making a product according to the color of the selected comparison sample.

The providing the system may include providing the system via a physical medium. The providing also may comprise providing the system in digital form configured to be printed using a digital information printing device.

The selecting of the at least one comparison sample may comprises determining which of the plurality of comparison samples substantially corresponds to a color the keratinous element to which the product is intended to be applied. The selecting of the at least one comparison sample may comprise determining which of the comparison samples substantially corresponds to a color desired by a user of the product.

Each comparison sample may comprise an identifier associated with the color of the sample, and the making of the product may be based on the identifier of the selected comparison sample.

Yet another aspect includes a method of monitoring the tanning of the skin. The method may comprise providing a system of comparison samples, selecting a comparison sample that substantially corresponds to a color of the skin to be monitored and exposing the skin to one of ultraviolet radiation, self-tanning lotion, and photosensitizing lotion. The method may further comprise determining whether the color of the skin has changed by comparing the skin with the comparison samples of the system.

The selection of the tanning regime may be based on the selected comparison sample. For example, the selection may be based on an identifier associated with the selected comparison sample.

According to yet another aspect, the invention includes a method of monitoring treatment of a keratinous element with a product. The method may comprise providing a system of comparison samples, selecting a comparison sample that substantially corresponds to a color of the keratinous element, and applying a product to the keratinous element. The method may further comprise determining whether the color of the keratinous element has changed after applying the product by comparing the keratinous element with the comparison samples of the system.

The method may further comprise exposing the keratinous element to ultraviolet radiation prior to determining whether the color of the keratinous element has changed.

In yet another aspect, a method of selecting a product for application to a keratinous element comprises providing a system of comparison samples, selecting a comparison sample of the system having a color that substantially corresponds to the keratinous element to which product is to be applied, and selecting a product from a plurality of differing products for application to the keratinous element based on the selected comparison sample.

Yet another aspect of the invention includes a method for treating a keratinous element comprising providing a system of comparison samples, selecting a comparison sample that corresponds to a desired color for the keratinous element, and treating the keratinous element based on the selected comparison sample. The treating may comprise applying a product to the keratinous element, wherein the product may be selected from a plurality of differing products.

According to an exemplary embodiment, each of the comparison samples may comprise an identifier that matches an identifier on each of a plurality of differing products. The selecting of the product may comprise selecting the product whose identifier matches the identifier of the selected comparison sample.

According to yet another aspect, the invention may include a method of manufacturing packaging for a product comprising providing at least one comparison sample having a reflectance spectrum and being configured to substantially simulate the color of a keratinous element having a reflectance spectrum and providing the at least one comparison sample on packaging for a product intended for application to the keratinous element. The reflectance spectrum of the at least one comparison element may be substantially similar to the reflectance spectrum of the keratinous element such that the comparison sample and the keratinous element appear to an observer to have substantially the same color under at least two differing illuminants.

The comparison samples may be affixed to the packaging or may be printed on the packaging.

The invention also may include the use of the system described above to determine the state of health of an individual, for example, by using the chart to detect any abnormal variation in the skin color of the individual, such as variation that may be characteristic of an unhealthy condition.

Yet another aspect includes a method of enabling analysis of a keratinous element. The method may comprise transmitting at least one image having a reflectance spectrum and being configured to substantially simulate a color of a keratinous element having a reflectance spectrum. The reflectance spectrum of the image may be substantially similar to the reflectance spectrum of the keratinous element such that the at least one image and the keratinous element appear to an observer to have substantially the same color under at least two differing illuminants.

The method may also comprise comparing the keratinous element to be analyzed with the at least one image to determine if the at least one image substantially corresponds to the color of the keratinous element.

The transmitting of the image may comprise transmitting the image via a network. The method may further comprise receiving information relating to a comparison between the keratinous element and the at least one image.

Transmitting an image may involve transmissions of the image through one or more networks and/or storage media. Networks may include public networks such as the Internet, telephoning networks, courier networks (e.g. postal service, United Parcel Service, Federal Express, etc.), private networks, or any other mechanisms for permitting communication between remote sites, regardless of whether the connection is wired or wireless. In a broader sense, an image may be transmitted physically such as in hard copy form, via mail delivery or other courier delivery. Storage media may include magnetic storage devices, such as floppy disks and hard drives; optical storage devices, such as compact discs and digital video discs; organic storage device; random access memory; printed media; or any other medium for storing information.

The keratinous element may be chosen from hair, skin, a fingernail, and a toenail, for example. The products for application to the keratinous element may be chosen from at least one of a cosmetic product and a care product. For example, the product may be chosen from a foundation makeup product, a concealer product, a lip makeup product, a hair coloring product, a hair care product, a nail varnish, a blush, an eyeshadow, a skin coloring product, such as a self-tanning lotion, for example, and a skin care product, such as a sun protection cream, for example.

The term "providing" is used broadly herein, and refers to, but is not limited to, making available for use, giving, supplying, obtaining, getting a hold of, acquiring, purchasing, selling, distributing, possessing, manufacturing, assembling, making ready for use, and/or placing in a position ready for use.

Besides the structural and procedural arrangements set forth above, the invention could include a number of other arrangements, such as those explained hereinafter. It is to be understood that both the foregoing description and the following description are exemplary. The accompanying drawings are provided to further the understanding of the invention and are incorporated in and constitute a part of this specification. The drawings illustrate exemplary embodiments of the invention and, together with the description, serve to explain certain principles. In the drawings, FIG. 1 is a perspective view of an exemplary embodiment of a system of comparison samples;

FIG. 4 is a view of an exemplary embodiment of a comparison sample in use for comparison to a person's skin;

FIG. 5 is an exemplary graph showing the reflectance spectrum of a particular keratinous element and a reflectance spectrum of a comparison sample that substantially simulates the skin;

FIG. 6 is a partial cross-sectional view of an exemplary embodiment comparison sample comprising reliefs;

FIG. 7 is a partial cross-sectional view of an exemplary embodiment of a comparison sample comprising gloss varnish;

FIG. 8 is a partial cross-sectional view of an exemplary embodiment of a comparison sample comprising mat varnish;

FIG. 9 is a partial cross-sectional view of an exemplary embodiment of a comparison sample comprising mat varnish and gloss varnish;

FIG. 10 is a schematic representation of an exemplary embodiment of a network system for displaying or printing comparison samples;

FIG. 11 is a plan view of an exemplary embodiment of a support in the form of a strip having five comparison samples therein; and FIG. 12 is a plan view showing an exemplary embodiment of a coating to obtain way in which regions of differing brightnesses.

Reference will now be made in detail to exemplary embodiments, examples of which are illustrated in the accompanying drawings. Wherever possible, the same reference numbers are used in the drawings and the description to refer to the same or like parts.

FIG. 1 shows a system 1, which may be in the form of a matching chart, comprising a plurality of comparison samples 4 each substantially simulating a skin color.

Each comparison sample 4 in the example described comprises a support covered in a colored coating.

Further, each comparison sample comprises a support that is substantially rectangular in shape, having dimensions close to 60 mm by 100 mm in the example described. Although the comparison sample in the example shown is rectangular, one having skill in the art would understand that the comparison sample 4 could have other configurations such as, but not limited to, elliptical, oblong, oval, triangular, rectangular, square, and polygonal, or combinations thereof.

Figure 1:
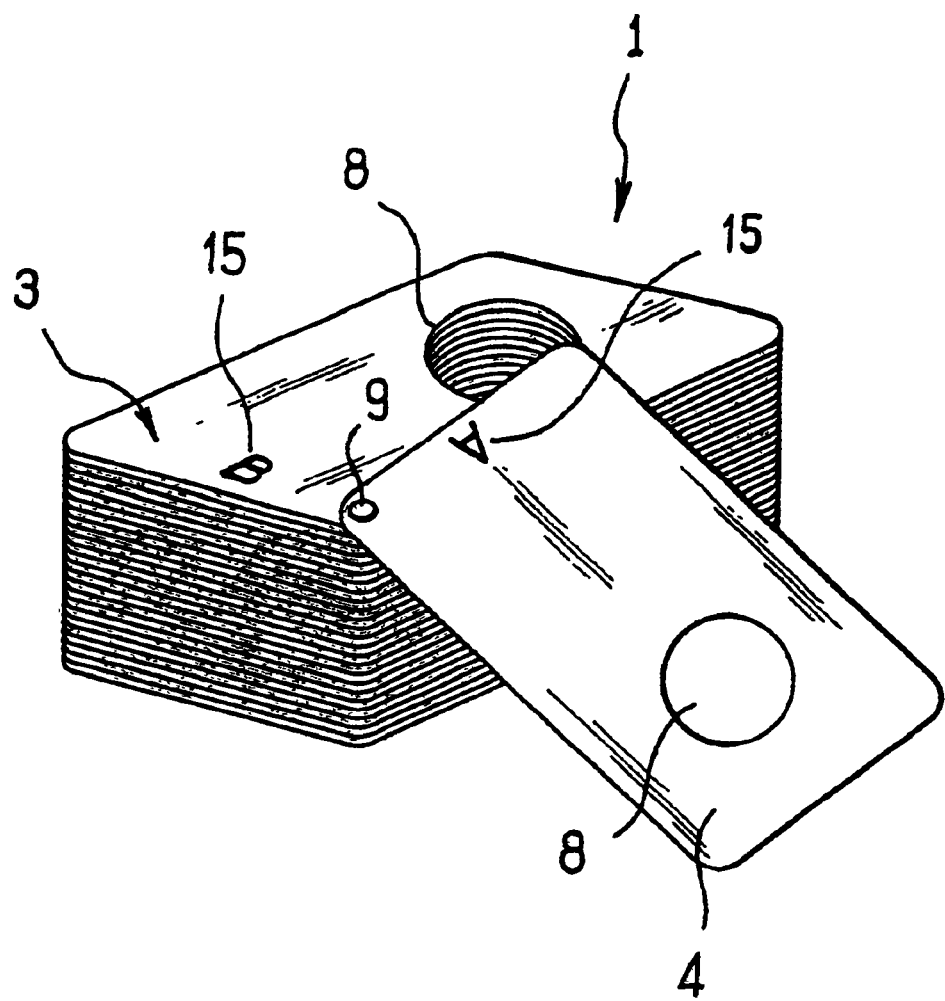

Each comparison sample 4, as shown in FIG. 1 may have a hole 8 passing therethrough. The hole may be circular and about 20 mm in diameter, and may be located at about one-third of the way along the length of the sample support. Although the hole 8 in the example shown is circular, one having skill in the art would understand that the hole 8 could have other configurations such as, but not limited to, elliptical, oblong, oval, triangular, rectangular, square, and polygonal, or combinations thereof.

The comparison sample 4 may be placed on a portion of the body or the face, including the lips, to compare the color of the sample to the color of the skin. As an example, in FIG. 4, the sample is placed on the forearm A.

The hole 8 permits an observer to observe simultaneously the appearance of the skin and the appearance of the comparison sample 4. This may facilitate comparison.

Compared with a square or a circular shape, a comparison sample 4 having a rectangular shape may permit the sample 4 to be oriented in a particular direction when it is in use. This may be preferable when the comparison sample imitates the texture of the skin, since skin texture is anisotropic.

Each comparison sample 4 may include an identifier 15 constituted by one or more alphanumeric characters, for example.

In the example described, the system 1 comprises fifty comparison samples 4 corresponding to fifty different skin colors. In this case, all of the comparison samples 4 have substantially the same brightness and substantially the same texture. The fifty colors may result, as in this example, from combining five hues with ten levels of lightness. Other combinations also may be provided as discussed.

The hue angles (h) measured in the CIEL*C*h 1976 color space may range from about 40° to about 70°, and/or from about 46° to about 64°.

In the example described, the lightness levels L* in the CIEL*C*h 1976 color space may range from about 25 to about 80, and/or from about 30 to about 70.

According to an example, the chroma levels of the samples may range from about 12 to about 30, and/or they are about 22.

The comparison samples 4 can be connected together in a fan-like configuration by being hinged about a pin 9, as shown in FIG. 1. Alternatively, they may be connected together so as to form a set by means of loops 15, as shown in FIGS. 2 and 3, for example.

The comparison samples 4 of the system can be grouped together in various ways. For example, all of the comparison samples 4 can be connected together in a single set 3, as shown in FIG. 1.

It also is possible to make up a plurality of sets so as to make the comparison samples 4 easier to handle.

Figure 2:
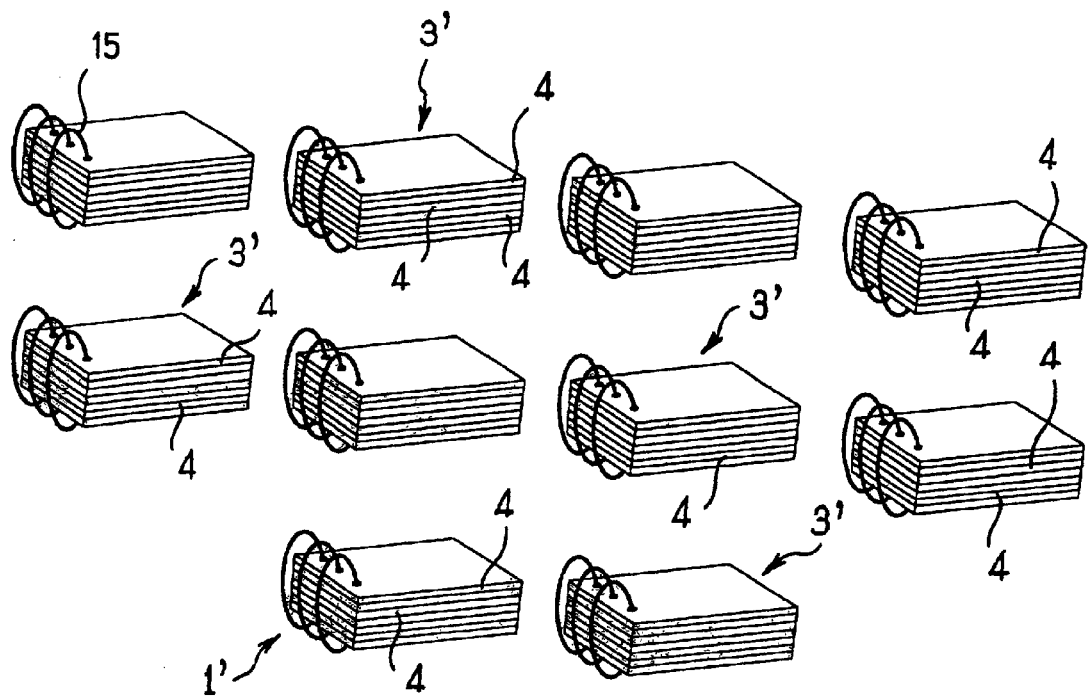
FIG. 2 is a perspective view of another exemplary embodiment of a system of comparison samples in the form of sets of samples.
Figure 3:
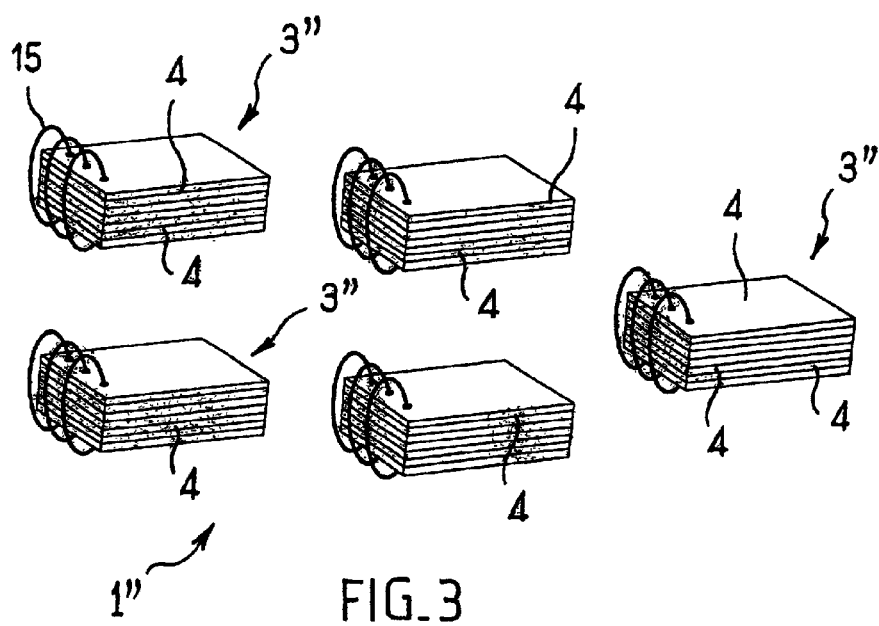
FIG. 3 is a perspective view of yet another exemplary embodiment of a system of comparison samples in the form of sets of samples.

The exemplary embodiment of the system 1' shown in FIG. 2 comprises ten sets 3' each corresponding to a determined hue, that differs from the hues of the other sets. Each set 3' may comprise five comparison samples 4 having differing lightness levels, but all having the same hue.

The exemplary embodiment of the system 1" shown in FIG. 3 comprises five sets 3" each corresponding to a determined hue that differs from the hues of the other sets. Each set 3" comprises ten comparison samples 4 of different lightnesses, but all of the same hue.

Of course, the groupings in FIGS. 2–3 are exemplary and other groupings also may be implemented without going beyond the ambit of the present invention.

By way of example, FIG. 11 shows five comparison samples provided on a common support in the form of a strip. These five comparison samples may all have substantially the same hue, for example, and may have differing lightnesses. Alternatively, they may all have substantially the same lightness, but have with differing hues.

The visual color difference as measured in the CIEL*C*h 1976 color space between two adjacent color comparison samples 4 may be constant, for example, equal to about four. The value may permit an untrained person easily to perceive a variation of color between two comparison samples 4.

The comparison samples 4 may enable skin color to be substantially simulated regardless of the illuminant. In particular, the comparison sample 4 may substantially simulate the skin color regardless of whether the illuminant is provided by daylight or artificial lighting of the incandescent or the fluorescent type, for example.

In general, it may be desirable to provide a reflectance spectrum of the comparison sample that corresponds as closely as possible to that of the corresponding skin in the wavelength range 400 nm to 800 nm.

The comparison samples 4 may thus be made on the basis of knowledge concerning the reflectance spectra of all varieties of skin color, including, for example, Caucasian skin, Black skin, or Asiatic skin.

By way of example, the continuous line in FIG. 5 shows the reflected relative intensity $I_R^{REF}$ (in %) as a function of wavelength (in nm) for a given skin type. The dashed line shows the reflective relative intensity $I_R^{MOD}$ (in %) as a function of wavelength (in nm) for a corresponding comparison sample.

Preferably, Δ, i.e.

$$1/N(\lambda)\sum_{\lambda}|I_R^{MOD}(\lambda) - I_R^{REF}(\lambda)|/I_R^{REF}$$

is less than or equal to 0.1, and/or less than or equal to 0.05, and/or less than or equal to 0.01.

It is possible to give precedence to spectral sub-ranges in which the reflectance of the comparison sample 4 and the corresponding skin may be substantially closer, for example, in which Δ is much smaller. For example, particular preference can be optionally given to the spectral range from about 600 nm to about 750 nm, corresponding to red and its various shades. By way of example, Δ can be less than or equal to about 0.01 in this spectral range.

To obtain a desired reflectance spectrum for each comparison sample 4, it is possible to use known software that enables a composition of pigments to be determined that corresponds to a given reflectance spectrum. For example, it is possible to use Datamatch software from Datacolor International.

The color of the comparison samples 4 can be substantially uniform. Alternatively, the comparison samples 4 can be made to each present a color that is non-uniform. For example, the comparison samples may have local variations in hue and/or in lightness.

In cases of color non-uniformity, the spectral reflectance of a comparison sample 4 may correspond to a mean value, for example, for an area having a diameter of 1 centimeter (cm).

Patterns can be made on the comparison samples 4 so as to imitate skin texture, for example. Each comparison sample 4 may have areas of differing hues and/or lightnesses. This may be obtained by printing patterns of a color that differs from that of the color of the background, which may be a sepia color.

It also may be possible to imitate the appearance of the skin by using a medium (e.g., support) that presents relief. As an example, a medium that has been embossed so as to imitate skin grain may be used. Embossing can be performed by calendering, for example, either before or after the color coating has been deposited.

To imitate skin appearance better, and optionally also to imitate its locally more or less shiny character, it may be desirable to confer non-uniform brightness on the comparison samples 4. There are various ways in which non-uniform brightness can be obtained. For example, it is possible to make plateaus 10 or recesses 11, as shown in FIG. 6.

Areas of color coating that match the shape of the recesses 11 then may appear to be less shiny than those covering the plateaus 10. Also, it is possible to apply gloss varnish to the plateaus 10, but not to the recesses 11.

It also may be possible to obtain non-uniform brightness by applying a gloss varnish 12 onto a plane medium, as shown in FIGS. 7 and 12. In this case, the varnish covers only a portion of the comparison sample, for example, the varnish may cover square shapes having side dimensions of approximately L=300 μm. These squares may be spaced apart from one another by distances of approximately d=100 μm.

In a variant, as shown in FIG. 8, it is possible to apply a mat varnish 13, for example, in the form of areas that are about 100 μm wide, and that are spaced apart from each other by a distance of about 300 μm.

It also is possible to juxtapose or superpose a gloss varnish and a mat varnish. As shown in FIG. 9, the regions 12 of gloss varnish may be about 300 μm wide and the regions 13 of mat varnish may be about 100 μm.

The exemplary systems shown in FIGS. 1, 2, and 3 can comprise comparison samples having a characteristic of appearance other than color that varies from one sample to another.

For example, brightness can vary from one sample to another so as to represent the fact that some skins are greasier than others.

Under such circumstances, the user of the system can determine not only skin color but also the brightness that corresponds thereto.

Other appearance characteristics also may vary within each sample. Examples of such appearance characteristics include relief or distribution of brightness or of color.

The system can be used in numerous situations, in particular in the field of cosmetics.

The system may be useful for performing statistical studies in a population, for example, to extract typological characteristics of certain skin types.

The system also may enable people to determine their skin colors. This may subsequently facilitate the purchase of cosmetics, especially foundation makeup, since people can then select makeup that has been given the same identifier as that provided on the comparison sample substantially corresponding to the persons skin color. This may help to ensure the person has chosen the right make-up color.

The system can also be useful when a person is seeking to apply a substance that does not correspond exactly to that person's own skin color, but that presents different lightness and/or hue, corresponding to a given comparison sample. Under such circumstances, and from the relative color of this comparison sample and the comparison sample corresponding to the skin color of the user, the user can determine how a color of interest is situated in terms of lightness and hue relative to the color of the user's own skin.

The system of the invention also may be used to determine variation in skin color, for example, after following treatment by a product, such as a skin coloring (e.g., self-tanning) product, for example, or merely following exposure to the sun or to an artificial source of ultraviolet radiation. The system may make it possible to determine whether a desired degree of suntan has been reached for a given person. If it has, that person can be informed that there is no need for any further exposure, thus enabling excessive exposure to be avoided or sun protection to be adopted.

As an example, before exposing the skin, the user may match his or her current skin color to a comparison sample. After exposure, the person may again match his or her skin to a comparison sample to determine whether the skin has become darker in color. Also, the person may pick a comparison sample having a desired or recommended color. The person may expose his or her skin until its color becomes substantially similar to the selected sample.

The system further may can also be used to determine the effect of a cosmetic or care product on the color of the skin, such as, for example, a self-tanning lotion, a foundation or other make-up product. Under such circumstances, the user can determine the effectiveness of the treatment by making a comparison with a comparison sample used as a reference and corresponding to the color of the skin before treatment begins.

The chart can be made available in physical form as shown in FIGS. 1 to 3. However, it would not go beyond the ambit of the present invention for the comparison samples to be supplied to the user in a non-physical form, such as in the form of a computer data file containing the information required to enable comparison samples to be printed or displayed on an appropriate medium, such as a monitor, for example.

By way of example, FIG. 10 shows a computer data file being transferred from a first computer 20 to a second computer 21, the file containing information for printing various comparison samples from a suitable printer 22. Data can be transmitted between the computers 20 and 21 by means of a computer network, for example, the Internet, an intranet, or a local area network.

As discussed above, transmitting an image may involve transmission of the image through one or more networks and/or storage mediums. Networks may include public networks such as the Internet, telephony networks, courier networks (e.g. postal service, United Parcel Service, Federal Express, etc.), private networks, virtual private networks, local area networks, metropolitan area networks, wide area networks, ad hoc networks, or any other mechanism for permitting communication between remote sites, regardless of whether the connection is wired or wireless. In a broader sense, an image may be transmitted physically such as in hard copy form, via mail delivery, or other courier delivery. Storage mediums may include magnetic storage devices, such as floppy disks and hard drives; optical storage devices, such as compact discs and digital video discs; organic storage devices; random access memory; printed media; or any other medium for storing information.

Naturally, the invention is not limited to the embodiments described above. It is possible to make comparison samples that substantially simulate the color of skin, including lips, a fingernail, a toenail, or hair of any determined type.

The various sizes and colors of the comparison samples and the described groupings thereof are exemplary and it should be understood that the comparison samples can be provided in a variety of different forms and can be grouped in numerous ways. Indeed, a single comparison sample may be provided. Further, a comparison sample may be supplied individually on a product that corresponds in some way to the comparison sample.

It will be apparent to those skilled in the art that various modifications and variations can be made to the structure and methodology. Thus, it should be understood that the invention is not limited to the examples and embodiments discussed in the specification. Rather, the present invention is intended to cover modifications and variations.

What is claimed is:

1. A matching chart comprising:
   a plurality of comparison samples having a reflectance spectrum and being configured to substantially simulate a color of a keratinous element having a reflectance spectrum,
   wherein at least one comparison sample comprises at least one of a pigment and a dye selected such that the reflectance spectrum of the comparison sample is substantially similar to the reflectance spectrum of the keratinous element such that the at least one comparison sample and the keratinous element appear to an observer to have substantially the same color under at least two differing illuminants.

2. The matching chart of claim 1, wherein at least one of the comparison samples is configured to be provided on packaging for a product.

3. The matching chart of claim 1, wherein the at least two differing illuminants are chosen from a D65 illuminant, a D50 illuminant, and an A illuminant.

4. the matching chart of claim 1, wherein the reflectance spectrum of the at least one comparison sample is substantially similar to the reflectance spectrum of the keratinous element in a spectral range from about 400 nm to about 800 nm.

5. The matching chart of claim 1, wherein the comparison sample is configured to substantially simulate a color of skin.

6. The matching chart of claim 1, wherein the comparison sample comprises at least one hue angle ranging from about 40° to about 70° in the CIEL*C*h 1976 color space.

7. The matching chart of claim 6, wherein the hue angle ranges from about 46° to about 64° in the CIEL*C*h 1976 color space.

8. The matching chart of claim 1, wherein the plurality of comparison samples comprises comparison samples having differing hues.

9. The matching chart of claim 8, wherein the plurality of comparison samples comprises comparison samples having at least five differing hues.

10. The matching chart of claim 1, wherein the plurality of comparison samples comprises comparison samples having differing levels of lightness.

11. The matching chart of claim 10, wherein the differing levels of lightness range from about 34 to about 75 in the CIEL*C*h 1976 color space.

12. The matching chart of claim 1, wherein the plurality of comparison samples comprises comparison samples having differing chroma levels.

13. The matching chart of claim 12, wherein the chroma levels range from about 12 to about 30.

14. The matching chart of claim 13, wherein at least one of the chroma levels is about 22.

15. The matching chart of claim 1, wherein the plurality of comparison samples comprises comparison samples having at least ten differing lightness levels.

16. The matching chart of claim 1, wherein at least one of the comparison samples is configured such that the color is substantially uniform and substantially constant over at least a portion of a surface of the comparison sample.

17. The matching chart of claim 1, wherein at least one of the comparison samples is configured such that the color is substantially uniform and substantially constant over the entire surface of the comparison sample.

18. The matching chart of claim 1, wherein the at least one of the comparison samples comprises a support.

19. The matching chart of claim 18, wherein the support has a substantially rectangular shape.

20. The matching chart of claim 19, wherein the support has a width of approximately 60 millimeters and a length of approximately 100 millimeters.

21. The matching chart of claim 1, wherein each comparison sample defines a hole configured to permit observation of the keratinous element through the hole.

22. The matching chart of claim 21, wherein the hole is located at about one third of the length of the comparison sample.

23. The matching chart of claim 21, wherein the hole has a dimension of approximately 20 millimeters.

24. The matching chart of claim 23, wherein the hole is circular and the dimension is a diameter.

25. The matching chart of claim 1, wherein at least one of the comparison samples comprises an identifier associated with the color of the sample.

26. The matching chart of claim 25, wherein the identifier is an alphanumeric code.

27. The matching chart of claim 1, wherein at least one of the comparison samples is configured to have a non-uniform brightness.

28. The matching chart of claim 27, wherein the at least one comparison sample comprises adjacent regions having differing brightnesses.

29. The matching chart of claim 27, wherein the at least one comparison sample comprises at least one relatively shiny region, the relatively shiny region comprising a gloss varnish.

30. The matching chart of claim 29, wherein a width of the relatively shiny region is approximately 300 micrometers.

31. The matching chart of claim 27, wherein the at least one comparison sample comprises a relatively dull region, the relatively dull region comprising a mat varnish.

32. The matching chart of claim 31, wherein a width of the relatively dull region is approximately 100 micrometers.

33. The matching chart of claim 1, wherein at least one of the comparison samples is further configured to simulate at least one appearance characteristic other than color of the keratinous element.

34. The matching chart of claim 33, wherein the at least one appearance characteristic other than color comprises brightness.

35. The matching chart of claim 33, wherein the at least one appearance characteristic other than color comprises relief.

36. The matching chart of claim 33, wherein the at least one appearance characteristic other than color comprises color non-uniformity.

37. The matching chart of claim 1, wherein at least one of the comparison samples comprises a relief pattern, the relief pattern being configured to provide a non-uniform brightness.

38. The matching chart of claim 1, wherein the plurality of comparison samples forms at least one set.

39. The matching chart of claim 38, wherein the plurality of comparison samples forming the at least one set are connected so as to form a fan-like configuration.

40. The matching chart of claim 1, further comprising a support, wherein the plurality of comparison samples are provided on the support.

41. The matching chart of claim 40, wherein the support is in the form of a strip.

42. The matching chart of claim 1, wherein the keratinous element is chosen from hair, skin, a fingernail, and a toenail.

43. A matching chart comprising:
at least one comparison sample having a reflectance spectrum and being configured to substantially simulate a color of a keratinous element having a reflectance spectrum,
wherein the at least one comparison sample comprises at least one of a pigment and a dye selected such that the reflectance spectrum of the comparison sample is substantially similar to the reflectance spectrum of the keratinous element such that the at least one comparison sample and the keratinous element appear to an observer to have substantially the same color under at least two differing illuminants,
wherein $$1/N(\lambda)\sum_{\lambda}|I_R^{MOD}(\lambda)-I_R^{REF}(\lambda)|/I_R^{REF}(\lambda)$$

is not greater than 0.1,
wherein $I_R^{MOD}(\lambda)$ is the reflected light intensity at wavelength $\lambda$ for the comparison sample and wherein $I_R^{REF}(\lambda)$ is the reflected light intensity at the wavelength $\lambda$ for the keratinous element.

44. The matching chart of claim 43, wherein $$1/N(\lambda)\sum_{\lambda}|I_R^{MOD}(\lambda)-I_R^{REF}(\lambda)|/I_R^{REF}(\lambda)$$

is not greater than 0.05.

45. The matching chart of claim 44, wherein:

$$1/N(\lambda)\sum_{\lambda}|I_R^{MOD}(\lambda)-I_R^{REF}(\lambda)|/I_R^{REF}(\lambda)$$

is not greater than 0.01.

46. A matching chart comprising:
a plurality of comparison samples having a reflectance spectrum and being configured to substantially simulate a color of a keratinous element having a reflectance spectrum,
wherein at least one comparison sample comprises at least one of a pigment and a dye selected such that the reflectance spectrum of the comparison sample is substantially similar to the reflectance spectrum of the keratinous element such that the at least one comparison sample and the keratinous element appear to an observer to have substantially the same color under at least two differing illuminants, and
wherein a total color difference $\Delta E^*C^*h.94$ measured in the CIEL*C*h 1976 color space between two comparison samples respectively substantially simulating two adjacent sample colors is substantially constant.

47. The matching chart of claim 46, wherein the total color difference ranges from about 1 to about 40.

48. The matching chart of claim 47, wherein the total color difference ranges from about 1 to about 20.

49. The matching chart of claim 48, wherein the total color difference is about 4.

50. A matching chart comprising:
at least one comparison sample having a reflectance spectrum and being configured to substantially simulate a color of a keratinous element having a reflectance spectrum,
wherein the at least one comparison sample comprises at least one of a pigment and a dye selected such that the reflectance spectrum of the comparison sample is substantially similar to the reflectance spectrum of the keratinous element such that the at least one comparison sample and the keratinous element appear to an observer to have substantially the same color Under at least two differing illuminants, and
wherein the at least one comparison sample is configured such that the color of the sample is nonuniform.

51. The matching chart of claim 50, wherein the at least one comparison sample comprises at least two color coatings, each color coating being a substantially different color.

52. A system comprising:
a plurality of comparison samples, each comparison sample having a reflectance spectrum and being configured to substantially simulate a color of a keratinous element having a reflectance spectrum,
wherein the reflectance spectrum of each comparison sample is substantially similar to the reflectance spectrum of a respective keratinous element such that the comparison sample and the keratinous element appear to an observer to have substantially the same color under at least two differing illuminants.

53. The system of claim 52, wherein the at least two differing illuminants are chosen from a D65 illuminant, a D50 illuminant, and an A illuminant.

54. The system of claim 52, wherein the reflectance spectrum of each comparison sample is substantially similar to the reflectance spectrum of the keratinous element in a spectral range from about 400 nm to about 800 nm.

55. The system of claim 52, wherein:

$$1/N(\lambda)\sum_{\lambda}|I_R^{MOD}(\lambda)-I_R^{REF}(\lambda)|/I_R^{REF}(\lambda)$$

is not greater than 0.1,
wherein $I_R^{MOD}(\lambda)$ is the reflected light intensity at wavelength $\lambda$ for the comparison sample and wherein $I_R^{REF}(\lambda)$ is the reflected light intensity at the wavelength $\lambda$ for the keratinous element.

56. The system of claim 52, wherein the comparison samples are configured to substantially simulate a color of skin.

57. The system of claim 52, wherein the comparison samples comprise hue angles ranging from about 40° to about 70° in the CIEL*C*h 1976 color space.

58. The system of claim 57 wherein the hue angles range from about 46° to about 64° in the CIEL*C*h 1976 color space.

59. The system of claim 52, wherein the comparison samples have differing hues.

60. The system of claim 59, wherein the plurality of comparison samples comprises comparison samples having at least five differing hues.

61. The system of claim 59, wherein the comparison samples have differing levels of lightness.

62. The system of claim 61, wherein the differing levels of lightness range from about 34 to about 75 in the CIEL*C*h 1976 color space.

63. The system of claim 52, wherein the comparison samples have differing chroma levels.

64. The system of claim 63, wherein the chroma levels range from about 12 to about 30.

65. The system of claim 64, wherein at least one of the chroma levels is about 22.

66. The system of claim 52, wherein the plurality of comparison samples comprise comparison samples having at least ten differing lightness levels.

67. The system of claim 52, wherein each comparison sample is configured such that the color of the each sample is substantially uniform and substantially constant over at least a portion of the surface of each comparison sample.

68. The system of claim 67, wherein each comparison sample is configured such that the color of each sample is substantially uniform and substantially constant over the entire surface of each comparison sample.

69. The system of claim 52, wherein each comparison sample comprises a support having a substantially rectangular shape.

70. The system of claim 69, wherein the support has a width of approximately 60 millimeters and a length of approximately 100 millimeters.

71. The system of claim 52, wherein each comparison sample defines a hole configured to permit observation of the keratinous element through the hole.

72. The system of claim 71, wherein the hole is located at about one third of the length of the comparison sample.

73. The system of claim 71, wherein the hole has a dimension of approximately 20 millimeters.

74. The system of claim 73, wherein the hole is circular and the dimension is a diameter.

75. The system of claim 52, wherein each comparison sample comprises an identifier associated with the color of each sample.

76. The system of claim 75, wherein the identifier is an alphanumeric code.

77. The system of claim 52, wherein each comparison sample is configured to have a nonuniform brightness.

78. The system of claim 77, wherein each comparison sample comprises adjacent regions having differing brightnesses.

79. The system of claim 77, wherein each comparison sample comprises at least one relatively shiny region, the relatively shiny region comprising a gloss varnish.

80. The system of claim 79, wherein a width of the relatively shiny region is approximately 300 micrometers.

81. The system of claim 77, wherein each comparison sample comprises a relatively dull region, the relatively dull region comprising a mat varnish.

82. The system of claim 81, wherein a width of the relatively dull region is approximately 100 micrometers.

83. The system of claim 52, wherein each comparison sample is further configured to simulate at least one appearance characteristic other than color of the keratinous element.

84. The system of claim 83, wherein the at least one appearance characteristic other than color comprises brightness.

85. The system of claim 84, wherein at least two comparison samples are configured to have differing brightnesses.

86. The system of claim 83, wherein the at least one appearance characteristic other than color comprises relief.

87. The system of claim 86, Wherein at least two comparison samples are configured to have differing degrees of relief.

88. The system of claim 83, wherein the at least one appearance characteristic other than color comprises color nonuniformity.

89. The system of claim 83, wherein each comparison sample comprises a relief pattern, the relief pattern being configured to provide a non-uniform brightness.

90. The system of claim 52, wherein the plurality of comparison samples forms at least one set.

91. The system of claim 90, wherein the plurality of comparison samples forming the at least one set are connected so as to form a fan-like configuration.

92. The system of claim 52, further comprising a support, wherein the plurality of the comparison samples are provided on the support.

93. The system of claim 92, wherein the support is in the form of a strip.

94. The system of claim 52, the keratinous element chosen from hair, skin, a fingernail, and a toenail.

95. The system of claim 52, wherein each comparison sample comprises at least one of a pigment and a dye.

96. The system of claim 52, wherein each comparison sample is configured to be displayed via an electronic image.

97. The system of claim 52, Wherein each comparison sample is configured to be respectively placed on a packaging for a product intended for application to the keratinous element.

98. A system comprising:
a plurality of comparison samples, each comparison sample having a reflectance spectrum and being configured to substantially simulate a color of a keratinous element having a reflectance spectrum,
wherein the reflectance spectrum of each comparison sample is substantially similar to the reflectance spectrum of a respective keratinous element such that the comparison sample and the keratinous element appear to an observer to have substantially the same color under at least two differing illuminants,
wherein $$1/N(\lambda) \sum_\lambda |I_R^{MOD}(\lambda) - I_R^{REF}(\lambda)| / I_R^{REF}(\lambda)$$

is not greater than 0.05,
wherein $I_R^{MOD}(\lambda)$ is the reflected light intensity at wavelength $\lambda$ for the comparison sample and wherein $I_R^{REF}(\lambda)$ is the reflected light intensity at the wavelength $\lambda$ for the keratinous element.

99. The system of claim 48, wherein $$1/N(\lambda) \sum_\lambda |I_R^{MOD}(\lambda) - I_R^{REF}(\lambda)| / I_R^{REF}(\lambda)$$

is not greater than 0.01.

100. A system comprising:
a plurality of comparison samples, each comparison sample having a reflectance spectrum and being configured to substantially simulate a color of a keratinous element having a reflectance spectrum,
wherein the reflectance spectrum of each comparison sample is substantially similar to the reflectance spectrum of a respective keratinous element such that the comparison sample and the keratinous element appear to an observer to have substantially the same color under at least two differing illuminants, and
wherein a total color difference $\Delta E^*C^*h.94$ measured in the CIEL*C*h 1976 color space between two comparison samples respectively substantially simulating two adjacent colors is substantially constant.

101. The system of claim 100, wherein the total color difference ranges from about 1 to about 40.

102. The system of claim 101, wherein the total color difference ranges from about 1 to about 20.

103. The system of claim 102, wherein the total color difference is about 4.

104. A system comprising:
a plurality of comparison samples, each comparison sample having a reflectance spectrum and being configured to substantially simulate a color of a keratinous element having a reflectance spectrum,
wherein the reflectance spectrum of each comparison sample is substantially similar to the reflectance spectrum of a respective keratinous element such that the comparison sample and the keratinous element appear to an observer to have substantially the same color under at least two differing illuminants, and
wherein each comparison sample is configured such that the color of the samples are nonuniform.

105. The system of claim 104, wherein each comparison sample comprises at least two color coatings, each color coating being a substantially different color.

106. A method of making a plurality of comparison samples configured to substantially simulate a color of a keratinous element, the method comprising:
depositing a coating on a support, the coating having a reflectance spectrum that is substantially similar to a reflectance spectrum of a keratinous element such that each comparison sample and the keratinous element appear to an observer to have substantially the same color under at least two differing illuminants.

107. The method of claim 106, wherein the reflectance spectrum of each comparison sample is substantially similar to the reflectance spectrum of the keratinous element in a spectral range from about 400 nm to about 800 nm.

108. The method of claim 106, wherein the at least two differing illuminants are chosen from a D65 illuminant, a D50 illuminant, and an A illuminant.

109. The method of claim 106, further comprising treating at least one of the support and the coating to imitate a texture of the keratinous element.

110. The method of claim 109, wherein the keratinous element is chosen from skin, hair, a fingernail, and a toenail.

111. The method of claim 109, wherein the treating comprises embossing.

112. The method of claim 109, wherein the treating comprises printing patterns on a background, wherein a color of the patterns differ from a color of the background.

113. The method of claim 109, wherein the treating comprises applying at least one of a mat varnish and a gloss varnish.

114. A method of manufacturing a product intended for application to a keratinous element, the method comprising:
providing the system of claim 52;
selecting at least one of the plurality of comparison samples; and
making a product intended for application to a keratinous element according to the color of the at least one selected comparison sample.

115. The method of claim 114, wherein the providing comprises providing the system via a physical medium.

116. The method of claim 114, wherein the providing comprises providing the system in digital form configured to be printed using a digital information printing device.

117. The method of claim 114, wherein the selecting of the at least one comparison sample comprises determining which of the plurality of comparison samples substantially corresponds to a color of the keratinous element to which the product is intended to be applied.

118. The method of claim 117, wherein the keratinous element is chosen from hair, skin, a fingernail, and a toenail.

119. The method of claim 114, wherein the selecting of the at least one comparison sample comprises determining which of the comparison samples substantially corresponds to a color desired by a user of the product.

120. The method of claim 114, wherein the product is chosen from at least one of a cosmetic product and a care product.

121. The method of claim 120, wherein the product is chosen from a foundation makeup product, a concealer product, a lip makeup product, a hair coloring product, a hair care product, a nail varnish, a blush, an eyeshadow, a skin coloring product, and a skin care product.

122. The method of claim 114, wherein the providing of the system comprises providing the plurality of comparison samples as a set.

123. The method of claim 117, wherein the determining which comparison sample substantially corresponds to the color of the keratinous element comprises placing the keratinous element adjacent to at least a portion of the comparison sample so as to permit comparison of the keratinous element with the comparison sample.

124. The method of claim 114, wherein each comparison sample comprises an identifier associated with the color of the sample, and wherein the making of the product further comprises making the product based on the identifier of the selected comparison sample.

125. The method of claim 124, wherein the identifier is an alphanumeric code.

126. The method of claim 114, wherein the at least two differing illuminants are chosen from a D65 illuminant, a D50 illuminant, and an A illuminant.

127. The method of claim 114, wherein the reflectance spectrum of each comparison sample is substantially similar to the reflectance spectrum of the keratinous element in a spectral range from about 400 nm to about 800 nm.

128. The method of claim 114, wherein the comparison samples are configured to substantially simulate a color of skin.

129. The method of claim 114, wherein the comparison samples comprise hue angles ranging from about 40° to about 70° in the CIEL*C*h 1976 color space.

130. The method of claim 114, wherein the comparison samples have differing hues.

131. The method of claim 114, wherein the comparison samples have differing levels of lightness.

132. The method of claim 131, wherein the differing levels of lightness range from about 34 to about 75 in the CIEL*C*h 1976 color space.

133. The method of claim 114, wherein the comparison samples have differing chroma levels.

134. The method of claim 133, wherein the chroma levels range from about 12 to about 30.

135. A method of manufacturing a product intended for application to a keratinous element, the method comprising:
providing a system comprising
a plurality of comparison samples, each comparison sample having a reflectance spectrum and being configured to substantially simulate a color of a keratinous element having a reflectance spectrum,
wherein the reflectance spectrum of each comparison sample is substantially similar to the reflectance spectrum of a respective keratinous element such that the comparison sample and the keratinous element appear to an observer to have substantially the same color under at least two differing illuminants;
selecting at least one of the plurality of comparison samples; and making a product intended for application to a keratinous element according to the color of the at least one selected comparison sample,
wherein $$1/N(\lambda) \sum_{\lambda} |I_R^{MOD}(\lambda) - I_R^{REF}(\lambda)| / I_R^{REF}(\lambda)$$

is not greater than 0.1,
wherein $I_R^{MOD}(\lambda)$ is the reflected light intensity at wavelength $\lambda$ for the comparison sample and wherein $I_R^{REF}(\lambda)$ is the reflected light intensity at the wavelength $\lambda$ for the keratinous element.

136. A method of manufacturing a product intended for application to a keratinous element, the method comprising:
providing a system comprising
a plurality of comparison samples, each comparison sample having a reflectance spectrum and being configured to substantially simulate a color of a keratinous element having a reflectance spectrum,
wherein the reflectance spectrum of each comparison sample is substantially similar to the reflectance spectrum of a respective keratinous element such that the comparison sample and the keratinous element appear to an observer to have substantially the same color under at least two differing illuminants;
selecting at least one of the plurality of comparison samples; and
making a product intended for application to a keratinous element according to the color of the at least one selected comparison sample,
wherein a total color difference $\Delta E^*C^*h.94$ measured in the CIEL*C*h 1976 color space between two comparison samples respectively substantially simulating two adjacent colors is substantially constant.

137. The method of claim 136, wherein the total color difference ranges from about 1 to about 40.

138. A method of monitoring tanning of skin, the method comprising:
providing the system of claim 52;
selecting a comparison sample that to substantially corresponds to a color of the skin to be monitored;
exposing the skin to one of ultraviolet radiation, self-tanning lotion, and photosensitizing lotion; and
determining whether the color of the skin has changed by comparing the skin with the comparison samples of the system.

139. The method of claim 138, wherein the comparing of the keratinous element with the comparison samples comprises placing the keratinous element adjacent to at least a portion of one of the comparison samples.

140. The method of claim 138, further comprising selecting a tanning regime based on the selected comparison sample.

141. The method of claim 140, wherein each of the comparison samples comprises an identifier associated with the color of the sample, and wherein the selecting of the tanning regime is based on the identifier of the selected comparison sample.

142. A method of monitoring treatment of a keratinous element with a product, the method comprising:
providing the system of claim 52;
selecting a comparison sample that substantially corresponds to a color of the keratinous element; p1 applying a product to the keratinous element; and
determining whether the color of the keratinous element to which the product has been applied has changed after applying the product by comparing the keratinous element with the comparison samples of the system.

143. The method of claim 142, further comprising exposing the keratinous element to ultraviolet radiation prior to determining whether the color of the keratinous element to which the product has been applied has changed.

144. The method of claim 142, wherein the product is at least one of a sun protection cream and a self-tanning lotion.

145. The method of claim 142, wherein the keratinous element is chosen from hair, skin, a fingernail, and a toenail.

146. The method of claim 142, further comprising selecting from a plurality of differing products the product to be applied to the keratinous element, wherein the selecting of the product is based upon the selected comparison sample.

147. The method of claim 146, wherein each of the comparison samples comprises an identifier associated with the color of the sample, and wherein each of the plurality of differing products comprises an identifier matching one of the identifiers of the comparison samples, and wherein the selecting of the product comprises selecting the product associated with the identifier that matches the identifier of the selected comparison sample.

148. The method of claim 147, wherein the identifier is an alphanumeric code.

149. The method of claim 142, wherein the product is chosen from a cosmetic product and a care product.

150. The method of claim 149, wherein the product is chosen from foundation makeup product, a concealer makeup product, a lip makeup product, a hair coloring product, a hair care product, a nail varnish, a blush, an eyeshadow, a skin coloring product, and a skin care product.

151. The method of claim 142, wherein the providing of the system comprises providing the plurality of comparison samples as a set.

152. The method of claim 142, wherein the comparing of the comparison samples with the keratinous element comprises placing the keratinous element adjacent to at least a portion of one of the comparison samples.

153. The method of claim 142, wherein the at least two differing illuminants are chosen from a D65 illuminant, a D50 illuminant, and an A illuminant.

154. The method of claim 142, wherein the reflectance spectrum of each comparison sample is substantially similar to the reflectance spectrum of the keratinous element in a spectral range from about 400 nm to about 800 nm.

155. The method of claim 142, wherein the comparison samples are configured to substantially simulate a color of skin.

156. The method of claim 142, wherein the comparison samples comprise hue angles ranging from about 40° to about 70° in the CIEL*C*h 1976 color space.

157. The method of claim 142, wherein the comparison samples have differing hues.

158. The method of claim 142, wherein the comparison samples have differing levels of lightness.

159. The method of claim 158, wherein the differing levels of lightness range from about 34 to about 75 in the CIEL*C*h 1976 color space.

160. The method of claim 142, wherein the comparison samples have differing chroma levels.

161. The method of claim 160, wherein the chroma levels range from about 12 to about 30.

162. A method of monitoring treatment of a keratinous element with a product, the method comprising:
providing a system comprising a plurality of comparison samples, each comparison sample having a reflectance spectrum and being configured to substantially simulate a color of a keratinous element having a reflectance spectrum, wherein the reflectance spectrum of each comparison sample is substantially similar to the reflectance spectrum of a respective keratinous element such that the comparison sample and the keratinous element appear to an observer to have substantially the same color under at least two differing illuminants;

selecting a comparison sample that substantially corresponds to a color of the keratinous element;

applying a product to the keratinous element; and determining whether the color of the keratinous element to which the product has been applied has changed after applying the product by comparing the keratinous element with the comparison samples of the system, wherein $$1/N(\lambda)\sum_{\lambda}|I_R^{MOD}(\lambda)-I_R^{REF}(\lambda)|/I_R^{REF}(\lambda)$$

is not greater than 0.1, wherein $I_R^{MOD}(\lambda)$ is the reflected light intensity at wavelength $\lambda$ for the comparison sample and wherein $I_R^{REF}(\lambda)$ is the reflected light intensity at the wavelength $\lambda$ for the keratinous element.

163. A method of monitoring treatment of a keratinous element with a product, the method comprising:

providing a system comprising a plurality of comparison samples, each comparison sample having a reflectance spectrum and being configured to substantially simulate a color of a keratinous element having a reflectance spectrum, wherein the reflectance spectrum of each comparison sample is substantially similar to the reflectance spectrum of a respective keratinous element such that the comparison sample and the keratinous element appear to an observer to have substantially the same color under at least two differing illuminants;

selecting a comparison sample that substantially corresponds to a color of the keratinous element;

applying a product to the keratinous element; and determining whether the color of the keratinous element to which the product has been applied has changed after applying the product by comparing the keratinous element with the comparison samples of the system, wherein a total color difference $\Delta E^*C^*h.94$ measured in the CIEL*C*h 1976 color space between two comparison samples respectively substantially simulating two adjacent colors is substantially constant.

164. The method of claim 163, wherein the total color difference ranges from about 1 to about 40.

165. A method of selecting a product for application to a keratinous element, the method comprising:

providing the system of claim 52;

selecting a comparison sample of the system having a color that substantially corresponds to the keratinous element to which product is to be applied; and selecting a product from a plurality of differing products for application to the keratinous element based on the selected comparison sample.

166. The method of claim 165, wherein each of the comparison samples comprises an identifier associated with the color of the sample, and wherein the selecting of the product is based on the identifier of the selected comparison sample.

167. The method of claim 166, wherein each of the plurality of products comprises an identifier that matches one of the identifiers of the comparison samples, and wherein the selecting of the product comprises selecting the product associated with an identifier that matches the identifier of the selected comparison sample.

168. The method of claim 165, wherein the product is chosen from a cosmetic product and a care product.

169. The method of claim 168, wherein the product is chosen from a foundation makeup product, a concealer product, a lip makeup product, a hair coloring product, a hair care product, a nail varnish, a blush, an eyeshadow, a skin coloring product, and a skin care product.

170. The method of claim 165, wherein the keratinous element is chosen from skin, hair, a fingernail, and a toenail.

171. The method of claim 166, wherein the identifier comprises an alphanumeric code.

172. The method of claim 165, wherein the product affects the color of the keratinous element.

173. The method of claim 165, further comprising comparing the keratinous element to the comparison samples to determine which comparison sample has a color that substantially corresponds to the keratinous element.

174. The method of claim 173, wherein the comparing comprises placing the keratinous element adjacent to at least a portion of the comparison sample.

175. The method of claim 165, further comprising providing each of the plurality of comparison samples on a respective packaging associated with each of the plurality of differing products.

176. The method of claim 165, wherein the at least two differing illuminants are chosen from a D65 illuminant, a D50 illuminant, and an A illuminant.

177. The method of claim 165, wherein the reflectance spectrum of each comparison sample is substantially similar to the reflectance spectrum of the keratinous element in a spectral range from about 400 nm to about 800 nm.

178. The method of claim 165, wherein the comparison samples are configured to substantially simulate a color of skin.

179. The method of claim 165, wherein the comparison samples comprise hue angles ranging from about 40° to about 70° in the CIEL*C*h 1976 color space.

180. The method of claim 165, wherein the comparison samples have differing hues.

181. The method of claim 165, wherein the comparison samples have differing levels of lightness.

182. The method of claim 181, wherein the differing levels of lightness range from about 34 to about 75 in the CIEL*C*h 1976 color space.

183. The method of claim 165, wherein the comparison samples have differing chrome levels.

184. The method of claim 183, wherein the chrome levels range from about 12 to about 30.

185. A method of selecting a product for application to a keratinous element, the method comprising:

providing a system comprising a plurality of comparison samples, each comparison sample having a reflectance spectrum and being configured to substantially simulate a color of a keratinous element having a reflectance spectrum, wherein the reflectance spectrum of each comparison sample is substantially similar to the reflectance spectrum of a respective keratinous element such that the comparison sample and the keratinous element appear to an observer to have substantially the same color under at least two differing illuminants;

selecting a comparison sample of the system having a color that substantially corresponds to the keratinous element to which product is to be applied; and selecting a product from a plurality of differing products for application to the keratinous element based on the selected comparison sample, wherein $$1/N(\lambda) \sum_\lambda |I_R^{MOD}(\lambda) - I_R^{REF}(\lambda)| / I_R^{REF}(\lambda)$$

is not greater than 0.1, wherein $I_R^{MOD}(\lambda)$ is the reflected light intensity at wavelength $\lambda$ for the comparison sample and wherein $I_R^{REF}(\lambda)$ is the reflected light intensity at the wavelength $\lambda$ for the keratinous element.

186. A method of selecting a product for application to a keratinous element, the method comprising:

providing a system comprising
a plurality of comparison samples, each comparison sample having a reflectance spectrum and being configured to substantially simulate a color of a keratinous element having a reflectance spectrum, wherein the reflectance spectrum of each comparison sample is substantially similar to the reflectance spectrum of a respective keratinous element such that the comparison sample and the keratinous element appear to an observer to have substantially the same color under at least two differing illuminants;

selecting a comparison sample of the system having a color that substantially corresponds to the keratinous element to which product is to be applied; and selecting a product from a plurality of differing products for application to the keratinous element based on the selected comparison sample, wherein a total color difference $\Delta E^*C^*h.94$ measured in the CIEL*C*h 1976 color space between two comparison samples respectively substantially simulating two adjacent colors is substantially constant.

187. The method of claim 186, wherein the total color difference ranges from about 1 to about 40.

188. A method of manufacturing packaging for a product, the method comprising:

providing a plurality of comparison samples having a reflectance spectrum and being configured to substantially simulate the color of a keratinous element having a reflectance spectrum; and providing at least one of the comparison samples on packaging for a product intended for application to a keratinous element, wherein the reflectance spectrum of the at least one comparison sample is substantially similar to the reflectance spectrum of the keratinous element such that the comparison sample and the keratinous element appear to an observer to have substantially the same color under at least two differing illuminants.

189. The method of claim 188, wherein the providing of at least one of the comparison samples on the packaging comprises affixing the at least one comparison sample to the packaging.

190. The method of claim 188, wherein the providing of at least one of the comparison samples on the packaging comprises printing at least one of the comparison samples on the packaging.

191. The method of claim 188, wherein the at least two differing illuminants are chosen from a D65 illuminant, a D50 illuminant, and an A illuminant.

192. The method of claim 188, wherein the reflectance spectrum of each comparison sample is substantially similar to the reflectance spectrum of the keratinous element in a spectral range from about 400 nm to about 800 nm.

193. The method of claim 188, wherein at least of the one comparison samples is configured to substantially simulate a color of skin.

194. The method of claim 188, wherein at least one of the comparison samples comprises hue angles ranging from about 40° to about 70° in the CIEL*C*h 1976 color space.

195. The method of claim 188, wherein there are a plurality of comparison samples substantially simulating differing colors of keratinous elements, and wherein the method further comprises providing each comparison sample on a packaging for a product.

196. The method of claim 195, wherein providing each comparison sample on a packaging comprises providing each comparison sample on respective packaging for differing products.

197. The method of claim 188, wherein the keratinous element is chosen from skin, hair, a fingernail, and a toenail.

198. The method of claim 188, wherein the packaging is for a product chosen from a cosmetic product and a care product.

199. A method of manufacturing packaging for a product, the method comprising:

providing at least one comparison sample having a reflectance spectrum and being configured to substantially simulate the color of a keratinous element having a reflectance spectrum; and providing the at least one comparison sample on packaging for a product intended for application to a keratinous element, wherein the reflectance spectrum of the at least one comparison sample is substantially similar to the reflectance spectrum of the keratinous element such that the comparison sample and the keratinous element appear to an observer to have substantially the same color under at least two differing illuminants, and wherein $$1/N(\lambda) \sum_\lambda |I_R^{MOD}(\lambda) - I_R^{REF}(\lambda)| / I_R^{REF}(\lambda)$$

is not greater than 0.1, wherein $I_R^{MOD}(\lambda)$ is the reflected light intensity at wavelength $\lambda$ for the comparison sample and wherein $I_R^{REF}(\lambda)$ is the reflected light intensity at the wavelength $\lambda$ for the keratinous element.

200. A method of treating a keratinous element, the method comprising:

providing the system of claim 52;

selecting a comparison sample from the system that corresponds to a desired color for the keratinous element, treating the keratinous element based on the selected comparison sample.

201. The method of claim 200, wherein the treating comprises applying a product to the keratinous element.

202. The method of claim 200, further comprising selecting a product for treating the keratinous element from a plurality of differing products based on the selected comparison sample.

203. The method of claim 202, wherein each comparison sample comprises an identifier associated with the color of the sample, and wherein the selecting of the product is based on the identifier of the selected comparison sample.

204. The method of claim 203, wherein each of the plurality of products comprises an identifier that matches one of the identifiers of the comparison samples, and wherein the selecting of the product comprises selecting the product associated with an identifier that matches the identifier of the selected comparison sample.

205. The method of claim 200, wherein the product is chosen from a cosmetic product and a care product.

206. The method of claim 205, wherein the product is chosen from a foundation makeup product, a lip makeup product, a hair coloring product, a hair care product, a nail varnish, a blush, an eyeshadow, a skin coloring product, and a skin care product.

207. The method of claim 200, wherein the keratinous element is chosen from hair, skin, a fingernail, and a toenail.

208. The method of claim 200, wherein the providing of the system comprises providing the plurality of comparison samples as at least one set.

209. The method of claim 202, further comprising providing each of the comparison samples on a respective packaging for each of the plurality of differing products.

210. The method of claim 200, wherein the at least two differing illuminants are chosen from a D65 illuminant, a D50 illuminant, and an A illuminant.

211. The method of claim 200, wherein the reflectance spectrum of each comparison sample is substantially similar to the reflectance spectrum of the keratinous element in a spectral range from about 400 nm to about 800 nm.

212. The method of claim 200, wherein $$1/N(\lambda) \sum_{\lambda} |I_R^{MOD}(\lambda) - I_R^{REF}(\lambda)| / I_R^{REF}(\lambda)$$

is not greater than 0.1,
wherein $I_R^{MOD}(\lambda)$ is the reflected light intensity at wavelength $\lambda$ for the comparison sample and wherein $I_R^{REF}(\lambda)$ is the reflected light intensity at the wavelength $\lambda$ for the keratinous element.

213. A method of enabling an analysis of a keratinous element, the method comprising:

transmitting at least one image having a reflectance spectrum and being configured to substantially simulate a color of a keratinous element having a reflectance spectrum, wherein the reflectance spectrum of the image is substantially similar to the reflectance spectrum of the keratinous element such that the at least one image and the keratinous element appear to an observer to have substantially the same color under at least two differing illuminants.

214. The method of claim 213, further comprising comparing the keratinous element to be analyzed with the at least one image to determine if the at least one image substantially corresponds to the color of the keratinous element.

215. The method of claim 213, wherein the transmitting of the image comprises transmitting the image via a network.

216. The method of claim 213, further comprising receiving information relating to a comparison between the keratinous element and the at least one image.

217. The method of claim 213, wherein the at least two differing illuminants are chosen from a D65 illuminant, a D50 illuminant, and an A illuminant.

218. The method of claim 213, wherein the reflectance spectrum of each comparison sample is substantially similar to the reflectance spectrum of the keratinous element in a spectral range from about 400 nm to about 800 nm.

219. The method of claim 213, wherein $$1/N(\lambda) \sum_{\lambda} |I_R^{MOD}(\lambda) - I_R^{REF}(\lambda)| / I_R^{REF}(\lambda)$$

is not greater than 0.1,
wherein $I_R^{MOD}(\lambda)$ is the reflected light intensity at wavelength $\lambda$ for the comparison sample and wherein $I_R^{REF}(\lambda)$ is the reflected light intensity at the wavelength $\lambda$ for the keratinous element.

* * * * *

UNITED STATES PATENT AND TRADEMARK OFFICE
CERTIFICATE OF CORRECTION

PATENT NO. : 6,985,230 B2
DATED : January 10, 2006
INVENTOR(S) : Jean De Rigal and Christophe Dauga It is certified that error appears in the above-identified patent and that said Letters Patent is hereby corrected as shown below:

Column 11,
Line 24, "the matching" should read -- The matching --.

Column 14,
Line 7, "Under" should read -- under --.
Line 49, "claim 57 wherein" should read -- claim 57, wherein --.

Column 15,
Line 59, "Wherein" should read -- wherein --.

Column 16,
Line 11, "claim 52, the keratinous element chosen" should read -- claim 52, wherein the keratinous element is chosen --.
Line 17, "Wherein" should read -- wherein --.

Column 19,
Line 66, delete "p1" and insert a paragraph break.

Column 24,
Line 8, "at least of the one" should read -- at least one of the --.

Signed and Sealed this

Fourth Day of April, 2006

JON W. DUDAS
*Director of the United States Patent and Trademark Office*